United States Patent
Durand (10) Patent No.: US 12,053,412 B2
(45) Date of Patent: Aug. 6, 2024

(54) OROPHARYNX APPLIANCE TO MAINTAIN AIRWAY PATENCY

(71) Applicant: Case Western Reserve University, Cleveland, OH (US)

(72) Inventor: Dominique M. Durand, Cleveland, OH (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 59 days.

(21) Appl. No.: 16/488,945

(22) PCT Filed: Feb. 28, 2018

(86) PCT No.: PCT/US2018/020165
§ 371 (c)(1),
(2) Date: Aug. 27, 2019

(87) PCT Pub. No.: WO2018/160660
PCT Pub. Date: Sep. 7, 2018

(65) Prior Publication Data
US 2020/0060866 A1    Feb. 27, 2020

Related U.S. Application Data (60) Provisional application No. 62/464,702, filed on Feb. 28, 2017, provisional application No. 62/516,863, (Continued)

(51) Int. Cl.
*A61F 5/56* (2006.01)
*A61B 5/08* (2006.01)
*A61B 5/00* (2006.01)

(52) U.S. Cl.
CPC .......... *A61F 5/566* (2013.01); *A61B 5/0826* (2013.01); *A61B 5/682* (2013.01)

(58) Field of Classification Search
CPC ....... A61F 5/566; A61B 5/0826; A61B 5/682; A61B 1/24; A61M 16/00; A61M 16/0495;
(Continued)

(56) References Cited

U.S. PATENT DOCUMENTS

| 3,132,647 A | 5/1964 | Corniello |
| 4,468,196 A * | 8/1984 | Keller ............... A61C 7/00 433/7 |

(Continued)

FOREIGN PATENT DOCUMENTS

| DE | 29603998 U1 | 7/1997 |
| EP | 2181678 A1 | 5/2010 |

(Continued)

OTHER PUBLICATIONS

Strollo Jr., Patrick J., et al. "Upper-airway stimulation for obstructive sleep apnea." New England Journal of Medicine 370.2 (2014): 139-149.

(Continued)

*Primary Examiner* — Ophelia A Hawthorne
*Assistant Examiner* — Michael Milo
(74) *Attorney, Agent, or Firm* — Tarolli, Sundheim, Covell & Tummino LLP (57) ABSTRACT

One aspect of the present disclosure relates to an oropharynx appliance that includes passive tongue retention structure (12) having an end portion (16) adapted to prevent a pharyngeal portion of a tongue of a subject from collapsing; and at least one anchoring structure (14, 148) that is connected to the passive tongue retention structure and adapted to secure the passive tongue retention structure to at least one tooth/mandible of the subject in a removable fashion. The passive tongue retention structure is sized and dimensioned so that the end portion prevents the posterior pharyngeal portion of the tongue from obstructing an orophar- (Continued)

ynx during sleep, without triggering a gag reflex, while still permitting the tongue to move during swallowing.

13 Claims, 9 Drawing Sheets

Related U.S. Application Data filed on Jun. 8, 2017, provisional application No. 62/567,358, filed on Oct. 3, 2017.

(58) Field of Classification Search
CPC .... A61M 2210/065; A61C 17/10; A22B 5/18; A61J 7/0061
USPC ........................................................ 128/848
See application file for complete search history.

(56) References Cited

U.S. PATENT DOCUMENTS

| | | | |
|---|---|---|---|
| 6,766,802 B1 | 7/2004 | Keropian | |
| 7,073,505 B2 | 7/2006 | Nelson et al. | |
| 7,658,192 B2 | 2/2010 | Harrington | |
| 7,770,582 B2 | 8/2010 | Chen et al. | |
| 7,861,722 B2 | 1/2011 | Keropian | |
| 7,963,286 B2 | 6/2011 | Burdumy | |
| 8,074,655 B2* | 12/2011 | Sanders ................ A61F 2/00 600/235 |
| 8,192,196 B2 | 6/2012 | Singh | |
| 8,251,069 B2 | 8/2012 | Burdumy et al. | |
| 8,302,609 B2 | 11/2012 | Martinez | |
| 8,464,709 B2 | 6/2013 | Wedemeyer | |
| 8,881,733 B1* | 11/2014 | Harkins ................ A61C 7/08 128/860 |
| 9,138,341 B2 | 9/2015 | Greenburg | |
| 9,204,991 B1 | 12/2015 | Harkins | |
| 9,254,219 B2 | 2/2016 | Shantha | |
| 9,421,073 B2 | 8/2016 | Makower et al. | |
| 9,492,310 B2 | 11/2016 | Makower et al. | |
| 9,675,494 B2 | 6/2017 | Zhang et al. | |
| 9,808,371 B2 | 11/2017 | Summer | |
| 9,833,353 B2 | 12/2017 | Witt et al. | |
| 2001/0027793 A1* | 10/2001 | Tielemans ............. A61F 5/56 128/848 |
| 2005/0236003 A1 | 10/2005 | Meader | |
| 2006/0130850 A1* | 6/2006 | Chen .................... A61F 5/566 128/860 |
| 2008/0041396 A1 | 2/2008 | Lucker | |
| 2008/0289637 A1 | 11/2008 | Wyss | |
| 2010/0043804 A1 | 2/2010 | Razmovski | |
| 2010/0139668 A1 | 6/2010 | Harrington | |
| 2010/0311008 A1 | 12/2010 | Gellerfors et al. | |
| 2011/0178439 A1 | 7/2011 | Irwin et al. | |
| 2011/0284011 A1 | 11/2011 | Mauclaire | |
| 2011/0297162 A1 | 12/2011 | Navarro Segura et al. | |
| 2012/0180798 A1* | 7/2012 | Begg .................... A61F 5/566 128/848 |
| 2012/0234332 A1 | 9/2012 | Shantha | |
| 2013/0125902 A1* | 5/2013 | Danielian ............. A61B 17/24 128/859 |
| 2013/0233324 A1* | 9/2013 | Witt .................. A61B 17/0401 128/848 |
| 2015/0223968 A1* | 8/2015 | Hervy .................. A61F 5/56 128/848 |
| 2015/0230970 A1* | 8/2015 | Kaner .................. A61F 5/566 128/848 |
| 2015/0238347 A1 | 8/2015 | Rosen et al. | |
| 2015/0342779 A1 | 12/2015 | Friedman et al. | |
| 2016/0278974 A1 | 9/2016 | Greenburg | |
| 2017/0325991 A1 | 11/2017 | Summer | |

FOREIGN PATENT DOCUMENTS

| | | | |
|---|---|---|---|
| EP | 2380533 A1 * | 10/2011 | ............ A61F 5/566 |
| EP | 2380533 A1 | 10/2011 | |
| JP | 200416632 A | 1/2004 | |
| WO | 2006/063403 A1 | 6/2006 | |
| WO | 2006070805 A1 | 7/2006 | |
| WO | 2008114832 A1 | 9/2008 | |
| WO | 2010/014726 A1 | 2/2010 | |
| WO | 2012/066464 A2 | 5/2012 | |
| WO | WO-2012066464 A2 * | 5/2012 | ............ A61F 5/566 |
| WO | 2018/098489 A1 | 5/2018 | |

OTHER PUBLICATIONS

Schwab, Richard J., et al. "Identification of upper airway anatomic risk factors for obstructive sleep apnea with volumetric magnetic resonance imaging." American journal of respiratory and critical care medicine 168.5 (2003): 522-530.

PCT International Search Report and Written Opinion for corresponding Application Serial No. PCT/US2018/020165, mailed Jun. 14, 2018, pp. 1-14.

Japanese Office Action for Corresponding Application Serial No. 2019-546859.

Chinese Office Action for corresponding Chinese Application Serial No. 201880014285.0, dated Apr. 2, 2021, pp. 1-14.

European Office Action for corresponding European Application Serial No. 18710286.8, dated Apr. 28, 2023, pp. 1-5.

\* cited by examiner

OROPHARYNX APPLIANCE TO MAINTAIN AIRWAY PATENCY

CROSS-REFERENCE TO RELATED APPLICATIONS

This application claims the benefit of U.S. Provisional Application No. 62/464,702, filed Feb. 28, 2017, entitled "TONGUE RETENTION PROSTHESIS FOR OBSTRUCTIVE SLEEP APNEA" and U.S. Provisional Application No. 62/516,863, filed Jun. 8, 2017, entitled "OROPHARYNX PROTECTION APPLIANCE." This application also claims the benefit of U.S. Provisional Application No. 62/567,358, filed Oct. 3, 2017, entitled "SYSTEMS AND METHODS FOR OBSTRUCTIVE SLEEP APNEA DETECTION AND MONITORING". These provisional applications are hereby incorporated by reference in their entirety for all purposes.

TECHNICAL FIELD

The present disclosure relates generally to obstructive sleep apnea and, more specifically, to an oropharynx appliance to maintain airway patency during sleep to prevent or treat obstructive sleep apnea.

BACKGROUND

Sleep apnea is a sleep disorder in which a sufferer has trouble breathing during sleep. This trouble breathing during sleep can lead to nocturnal hypoxemia and sleep fragmentation, which can lead to co-morbidities, like daytime sleepiness, as well as cardiac and neural complications. The most common type of sleep apnea is obstructive sleep apnea, affecting 27 million patients in the US alone. Obstructive sleep apnea is characterized by the recurrent collapse of soft tissue occluding the upper airway during sleep. The airway obstruction leads to pauses in breathing or instances of shallow or infrequent breathing that can happen many times during the night. Individuals with sleep apnea are rarely aware of their difficulty breathing, even upon awakening, leading to the associated poor diagnosis and treatment. In fact, no drug therapies exist to treat sleep apnea. Although several mechanical therapies exist, such as continuous positive airway pressure (CPAP) therapy or a mandibular advancement device (MAD) treatment, these therapies are often improperly used, poorly tolerated, and/or ineffective.

Summar

The present disclosure relates generally to obstructive sleep apnea and, more specifically, to an oropharynx appliance to maintain airway patency during sleep to prevent or treat obstructive sleep apnea.

In one aspect, the present disclosure can include an oropharynx appliance configured to maintain airway patency during sleep. The oropharynx appliance includes a passive tongue retention structure having an end portion adapted to prevent a pharyngeal portion of a tongue of a subject from collapsing. The oropharynx appliance can also include at least one anchoring structure that is connected to the passive tongue retention structure and adapted to secure the passive tongue retention structure within the subject's mouth in a removable fashion while allowing movement. The passive tongue retention structure is sized and dimensioned so that the end portion prevents obstruction of an oropharynx during sleep, without triggering a gag reflex, while still permitting the tongue to move during swallowing.

In another aspect, the present disclosure can include an oropharynx system that can maintain airway patency during sleep. The system can include an oropharynx appliance sized and dimensioned so that an end portion thereof prevents a pharyngeal portion of a tongue of a subject from obstructing an oropharynx during sleep, without triggering a gag reflex, while still permitting the tongue to move during swallowing. The system can also include an anchoring system configured to mate with the oropharynx appliance to secure a portion of the oropharynx appliance in a predefined anatomical position In a further aspect, the present disclosure can include a method for fitting an oropharynx appliance configured to maintain airway patency during sleep into a subject's mouth. Images can be taken of a subject's oral cavity. Based on the images, the oropharynx appliance can be fabricated. After fabrication, the oropharynx appliance can be fit into the subject's oral cavity.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "obstructive sleep apnea" can refer to a sleep disorder that is caused by complete or partial obstruction of a subject's airway, leading to repetitive episodes of shallow or paused breathing during sleep, despite the subject's effort to breathe. The obstruction can be due to a collapse of soft tissue into the oropharynx of the subject's upper airway.

As used herein, the term "mandible" can refer to the subject's lower jaw. Notably, the lower jawbone is the only moveable bone in the skull.

As used herein, the term "mouth" can refer to the structures enclosing or being within the oral cavity. The mouth can include a plurality of teeth and a tongue.

As used herein, the term "oral cavity" can refer to the cavity of the mouth, bounded by the upper and lower jawbones and the cheeks.

As used herein, the term "tongue" can refer to the fleshy muscular organ in a subject's mouth. The tongue can be composed of an anterior oral part and a posterior pharyngeal part. The posterior pharyngeal part can be the posterior third of the tongue that is part of the oropharynx.

As used herein, the term "oropharynx" can refer to a part of the throat behind the mouth. The oropharynx begins where the oral cavity stops and includes the posterior pharyngeal part of the tongue.

As used herein, the term "arcuate" can refer to a generally curved shape. Examples of arcuate shapes include an arc or a bow. However, in some instances, the arcuate shape can include one or more bent portions, linear portions, or another curvilinear configuration, as long as the general curvature exists.

As used herein, the term "spring" can refer to a resilient device that can be pressed or pulled but returns to its former shape when released. In some instances, a spring can be shaped in an at least partially helical manner. Example uses of a spring include exerting constant tension or absorbing movement.

As used herein, the term "appliance" can refer to a device designed to perform a specific task. The term "apparatus" may be used interchangeably with the term "appliance".

As used herein, the term "prevent" can refer to keeping something from happening or arising. For example, when worn by a subject who snores, the oropharynx appliance can prevent the subject from developing obstructive sleep apnea.

As used herein, the term "treat" can refer to healing or curing a medical disorder. As an example, when worn by a subject with obstructive sleep apnea, the oropharynx appliance can treat obstructive sleep apnea by preventing the collapse of the tongue or other soft tissue into the oropharynx.

As used herein, the term "wire" can refer to a metal, polymer, composite, or other material structure. In some instances, the cross-sectional area of the material structure can be constant. In other instances, the cross-sectional area of the material structure can be variable from at least one portion of the wire to another portion of the wire. The cross section of the wire can be circular, curved, rectangular, linear, flat, curvilinear, star, or any other shape.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

II. Overview

The present disclosure relates generally to the prevention or treatment of obstructive sleep apnea. The prevention or treatment can be accomplished with the assistance of an oropharynx appliance, a mechanical device to prevent airway occlusion during sleep due to the collapse of soft tissue (e.g., the tongue) into the oropharynx. In patients with sleep apnea, during sleep, the tongue muscles are relaxed and the tongue can be pulled into the oropharynx by the negative pressure generated during inspiration. The oropharynx appliance prevents the tongue from moving backwards into the oropharynx during sleep, thereby maintaining airway patency.

The oropharynx appliance can include a passive tongue retention structure that can prevent the tongue from moving backwards, and at least one anchoring structure adapted to secure the passive tongue retention structure within the subject's mouth in a removable fashion while allowing movement. The passive tongue retention structure can be designed to allow air to pass during sleep, without triggering a gag reflex, while still permitting the tongue to move during swallowing. For example, the passive tongue retention structure can be designed to stay within a plane parallel with the mandible. However, the passive tongue retention structure can also be positioned over the surface of the tongue.

III. Systems

One aspect of the present disclosure can include an oropharynx appliance to maintain airway patency during sleep to prevent or treat obstructive sleep apnea. The oropharynx appliance can be part of a system, shown in FIG. 1, that includes a dental device (e.g., mouth guard 148) to anchor the passive tongue retention structure 12 of the oropharynx apploance within a subject's mouth (e.g., a hook, a mouth guard, a retainer, or a crown). However, the oropharynx appliance does not need the dental devices and can instead be anchored by a device that is at least partially within the oropharynx appliance, such as a spring, a loop, or a hook. The oropharynx can also include other anchoring means, such as one or more magnets, hydraulics, electrostatics, or the like.

The oropharynx appliance employs a mechanical design that is configured to prevent airway occlusion during sleep. The mechanical design prevents the undesired collapse of soft tissue into the oropharynx, thereby maintaining airway patency. In some instances, the soft tissue can be the tongue. Muscles of the tongue relax during sleep, causing tissue of the tongue to be pulled into the oropharynx by negative pressure generated during inspiration and obstruct the airway. The mechanical device can prevent the tongue from moving backwards into the oropharynx during inspiration and obstructing the airway. Although an oropharynx appliance that can be situated behind the tongue in the oropharynx will be described throughout, it will be noted that other placements for the oropharynx appliance can be used, such as behind the soft palate in the nasopharynx. The oropharynx appliance need not be behind the tongue and, instead may be in any position that is adapted to prevent the pharyngeal portion of the tongue from collapsing.

Figure 2:
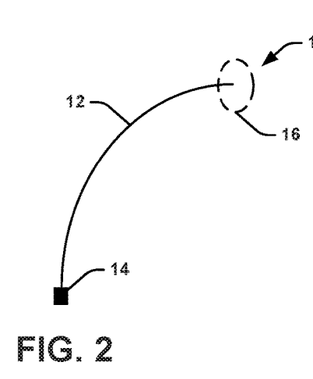
FIG. 2 is a schematic illustration showing an example of an oropharynx appliance configured to maintain airway patency during sleep to prevent or treat obstructive sleep apnea in accordance with an aspect of the present disclosure.

FIG. 2 shows an example of a mechanical device, shown and described herein as an oropharynx appliance 1, including a passive tongue retention structure 12 and an anchoring structure 14 that holds the passive tongue retention structure 12 in the subject's mouth. The oropharynx appliance 1 can extend from an anchor point (a tooth, as shown, or another area such as a portion of the gum, the tongue, or any other desired anchor point), along a lingual surface of the mandible and/or over the top surface of the tongue, and ultimately, behind at least a portion of the pharyngeal portion of the subject's tongue to prevent the portion of the tongue from collapsing into the throat.

In some instances, the passive tongue retention structure 12 can be maintained within a plane that is parallel with the mandible. In still other instances, the tongue retention structure 12 can extend over the surface of the tongue. In still other instances, the passive tongue retention structure can extend over, under, or around the tongue in any configuration as long as at least a portion of the passive tongue retention structure 12 extends behind at least a portion of the pharyngeal portion of the subject's tongue to prevent the pharyngeal portion of the tongue from collapsing into the throat. However, the passive tongue retention structure 12 need not be behind the tongue and, instead may be in any position that is adapted to prevent the pharyngeal portion of the tongue from collapsing.

Figure 1:
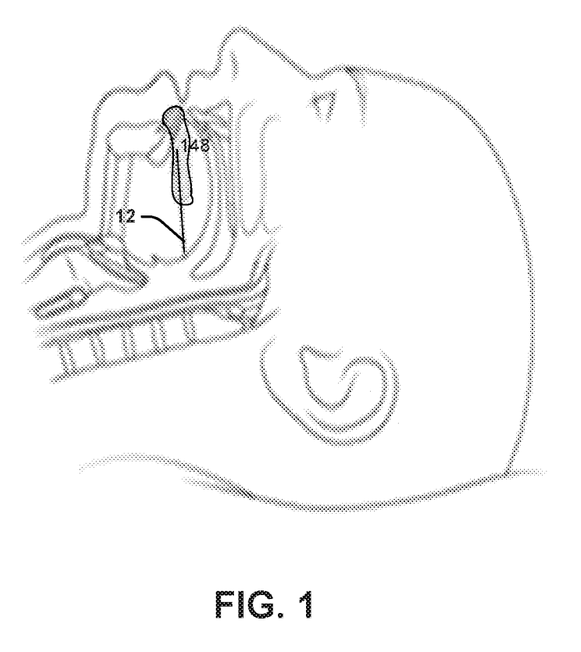
FIG. 1 is a schematic illustration showing an system that restrains the tongue from falling into the oropharynx.
Figure 3:
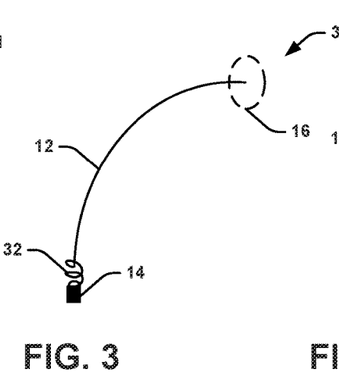
FIGS. 3-7 are schematic illustrations showing different examples of the oropharynx appliance of FIG. 1.
Figure 4:
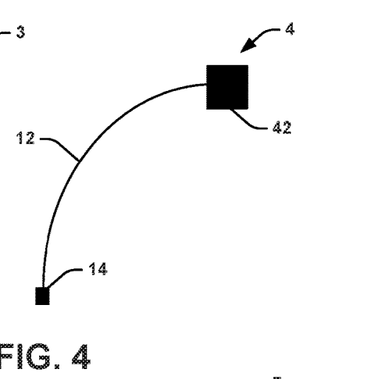

The oropharynx appliance 1 of FIG. 1, as well as oropharynx appliances 3 and 4 in FIGS. 3 and 4, is subject to several design considerations. The passive tongue retention structure 12 must prevent the tongue from moving backwards into the oropharynx, while also allowing movement of the tongue for swallowing. However, at least a portion of the passive tongue retention structure 12 must allow movement of the tongue, but prevent the passive tongue retention structure 12 from moving upwards or downwards into the oral cavity or oropharynx. Additionally, the portion of the passive tongue retention structure 12 must not generate a gag reflex and must not generate a significant amount of saliva (e.g., more than normally generated without the oropharynx appliance 1, 3, or 4).

In one aspect, the passive tongue retention structure 12 can be primarily constructed of a thin wire (made of metal, polymer, an organic material, or the like) that is stiff enough to prevent bending by the tongue. For example, the thickness and/or cross-sectional area of the wire can be nonconstant. Additionally, the wire can have a circular, curved, rectangular, linear, flat, curvilinear, or any other shaped cross section. The wire can be biocompatible to minimize irritation in the patient's mouth. Additionally, the wire can be durable and/or robust so that portions of the wire do not dislodge while the subject is sleeping. The wire can, in some instances, be constructed of a metal and/or polymer that is itself biocompatible or coated with a biocompatible material. As an example, the wire can have a ribbon-like form with a flat direction facing the tongue and the cheeks with at least one wiggle through the length (this eliminates the need for the spring shown in FIG. 3). The passive tongue retention structure 12 can include an end portion 16 that can be constructed of the same wire or a different biocompatible material. For example, the end portion can be arcuate.

In another aspect, the end portion 16 can be adapted to restrain all or at least a portion of the subject's tongue. The passive tongue retention structure 12 can be sized and dimensioned so that the end portion 16 prevents the posterior pharyngeal portion of the tongue from obstructing the subject's oropharynx during sleep, without triggering the gag reflex, while still permitting the tongue to move during swallowing. In some instances, the end portion 16 can include at least a rounded portion. In other instances, the end portion 16 can include one or more bends.

As shown in FIG. 4, the end portion 16 can include an engagement structure 42 that is configured to establish contact with the posterior pharyngeal portion of the tongue. In some instances, the engagement structure 42 can be larger than the rest of the passive tongue retention structure 12 to prevent the tongue from obstructing the oropharynx. For example, the engagement structure 42 can be in the form of: one or more wire coils of the same or different biocompatible material as the wire of the passive tongue retention structure 12; an additional portion of the same or different wire attached to the passive tongue retention structure 12; and/or a piece of material either the same as the wire or different from the wire. The engagement structure 42 can provide an additional portion to prevent the tongue from moving backwards into the oropharynx during inspiration and obstructing the airway, while not generating the gag reflex and not generating an excess amount of saliva.

The anchoring structure 14 can be adapted to secure the passive tongue retention structure 12 to at least one of the subject's teeth or a portion of the subject's mandible in a removable fashion. For example, the anchoring structure 14 can include one or more loops to secure the oropharynx appliance 1 to one or more teeth and/or portions of the mandible. In another example, the anchoring structure 14 can include a magnet configured to attach to a reciprocal magnetic member that is connected to a portion of the subject's mouth. In some instances, as shown in the oropharynx appliance 3 of FIG. 3, the anchoring structure 14 can include one or more springs 32. The one or more springs 32 can be configured to allow movement of the tongue for swallowing. Although illustrated separately, it will be appreciated that, in some instances, the one or more springs 32 and the engagement structure 42 can be used together in another example of the oropharynx apparatus of the present disclosure.

Figure 5:
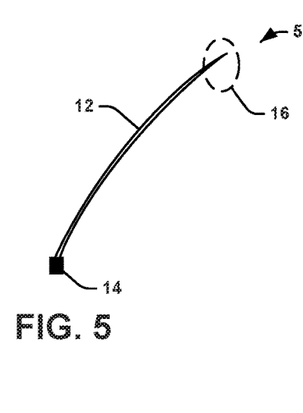

FIG. 5 shows an alternative configuration of an oropharynx appliance 5, in which the passive tongue retention structure 12 loops or bends back to the anchoring structure 14, increasing the strength of the passive tongue retention structure. In other words, the oropharynx appliance 5 can extend from an anchor point, along a lingual surface of the mandible, behind at least a portion of the posterior pharyngeal portion of the subject's tongue to contact the posterior pharyngeal portion of the subject's tongue, and then extend back along the lingual surface of the mandible, to again contact the anchor point. In some instances, the passive tongue retention structure 12 can stay within a plane that is parallel with the mandible. In other instances, the portion of the passive tongue retention structure 12 can run over an upper surface of the tongue.

Figure 6:
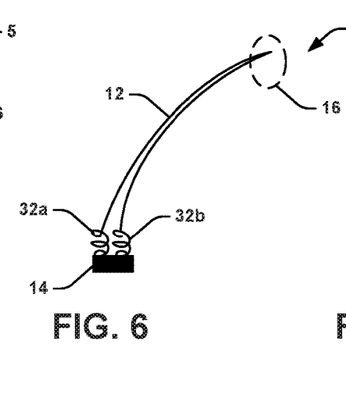
Figure 7:
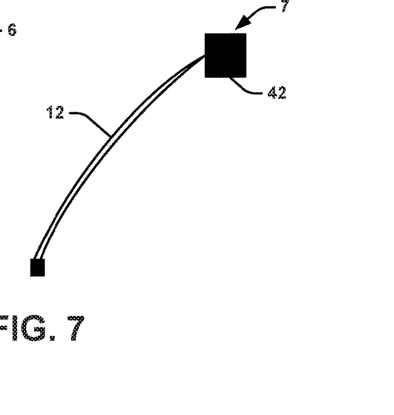

The oropharynx appliance 5 of FIG. 5, as well as oropharynx appliances 6 and 7 in FIGS. 6 and 7, is subject to several design considerations. The passive tongue retention structure 12 must prevent the tongue from moving backwards into the oropharynx, while also allowing movement of the tongue for swallowing. However, at least a portion of the passive tongue retention structure 12 must be attached so that movement of the tongue does not bring the passive tongue retention structure 12 upwards or downwards into the oral cavity or oropharynx. For example, the portion of the passive tongue retention structure 12 can remain in line with one or more of the subject's lower incisive teeth. Additionally, the portion of the passive tongue retention structure 12 must not generate a gag reflex and must not generate a significant amount of saliva (e.g., more than normally generated without the oropharynx appliance 5, 6, or 7).

In the oropharynx appliance 5 of FIG. 5, the thickness, cross-sectional shape, and/or stiffness of the passive tongue retention structure 12 must be well controlled to hold the tongue so that the tongue does not block the oropharynx while preventing a gag reflex, preventing the formation of excess saliva, and allowing movement of the tongue for swallowing.

FIG. 6 shows a further example of an oropharynx appliance 6 that can include two or more springs 32a and 32b. The two or more springs 32a and 32b can allow greater movement of the tongue for swallowing and stronger attachment of the passive tongue retention structure 12 to the anchoring structure 14. FIG. 7 shows a further example of an oropharynx appliance 7 that can include an engagement structure 42. Although the two or more springs 32a and 32b and the engagement structure 42 are illustrated as being used separately, it will be appreciated that the two or more springs 32a and 32b and the engagement structure 42 can be used together in the same oropharynx appliance. However, as an example, to eliminate the need for the springs 32a, 32b, the passive tongue retention structure 12 can have a ribbon-like form with a flat direction facing the tongue and the cheeks with at least one wiggle through the length.

Figure 8:
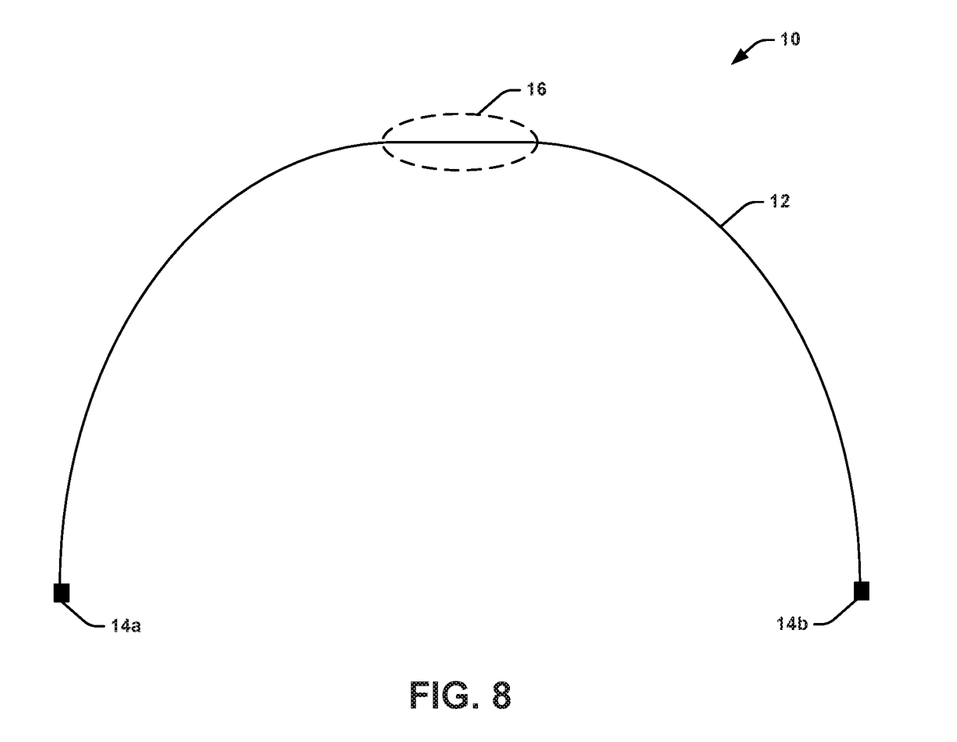
FIG. 8 is a schematic illustration showing an example of an oropharynx appliance to maintain airway patency during sleep to prevent or treat obstructive sleep apnea in accordance with another aspect of the present disclosure.

FIG. 8 shows an alternative configuration of an oropharynx appliance 10 in which the passive tongue retention structure 12 includes a portion (end portion 16) adapted to prevent the pharyngeal portion of the tongue from collapsing. The passive tongue retention structure 12 extends between bilateral anchoring structures 14a and 14b. The anchoring structures 14a and 14b can attach the passive tongue retention structure 12 to one or more teeth located bilaterally on the subject's lower jaw. However, at least one of the anchoring structures 14a and 14b can attach to a portion of the subject's lower jaw itself. Alternatively, at least one of the anchoring structures 14a and 14b can attach to a portion of the subject's tongue.

In some instances, the passive tongue retention structure 12 can stay within a plane that is parallel with the mandible. In other instances, a portion of the passive tongue retention structure 12 can extend over the top of the tongue. In further instances, the tongue retention structure can extend over, under, or around the tongue in any configuration as long as a portion of the passive tongue retention structure 12 prevents a pharyngeal portion of a tongue of a subject from collapsing.

The oropharynx appliance 10 of FIG. 8, as well as oropharynx appliances 30-70 in FIGS. 9-12, is subject to several design considerations. The passive tongue retention structure 12 must prevent the tongue from moving backwards into the oropharynx, while also allowing movement of the tongue for swallowing. However, at least a portion of the passive tongue retention structure 12 must prevent movement of the tongue from bringing the passive tongue retention structure 12 upwards or downwards into the oral cavity or oropharynx. For example, the portion of the passive tongue retention structure 12 can remain in line with one or more of the subject's lower incisive teeth. However, the passive tongue retention structure 12 is not required to be in line with the subject's lower incisive teeth. Additionally, the portion of the passive tongue retention structure 12 must not generate a gag reflex and must not generate a significant amount of saliva (e.g., more than normally generated without the oropharynx appliance 30-70) when preventing the portion of the pharyngeal portion of the tongue from collapsing into the oropharynx. For example, the passive tongue retention structure 12 can be of a thin, stiff wire with examples similar to that described with respect to the oropharynx appliance 1.

Figure 9:
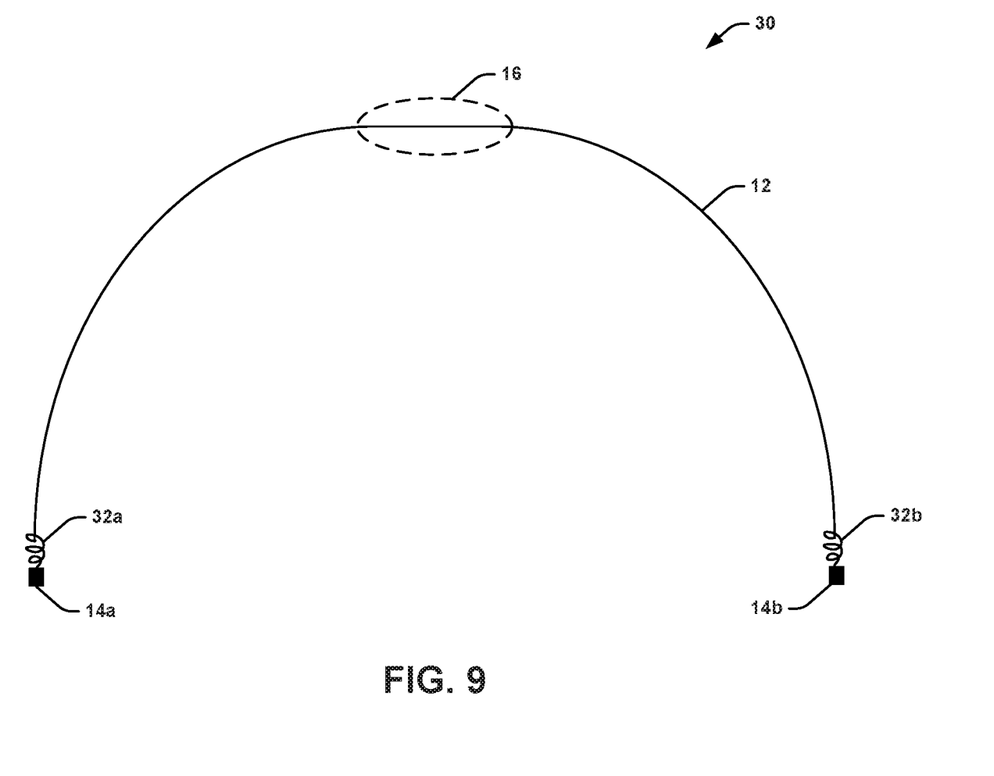
FIGS. 9-12 are a schematic illustrations showing different examples of the oropharynx appliance of FIG. 8.
Figure 10:
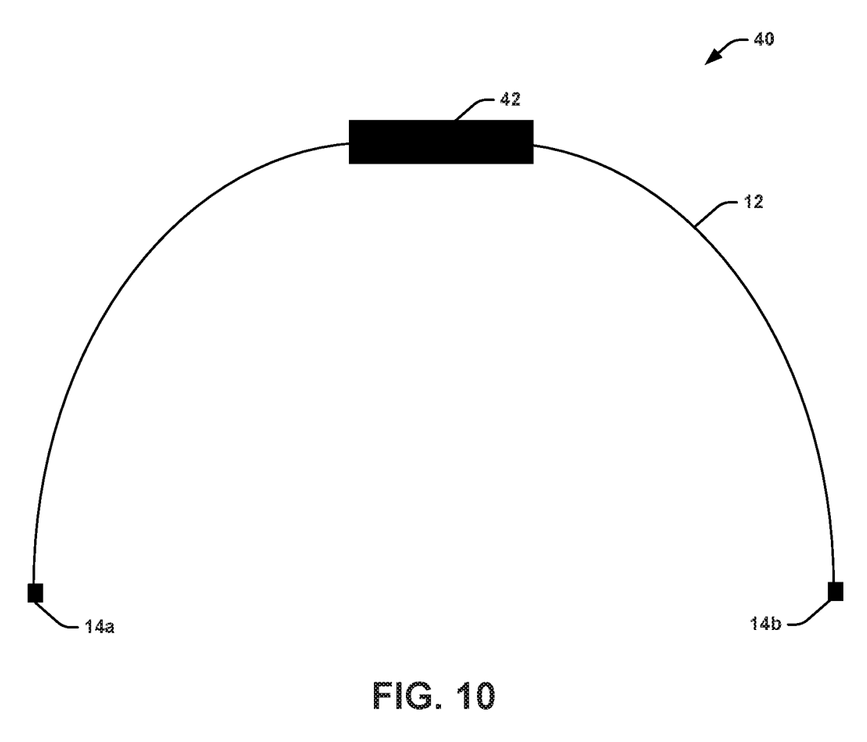

In one aspect, each anchoring structure 14a and 14b (FIG. 8) can be adapted to secure the passive tongue retention structure 12 to at least two of the subject's teeth and/or portions of the subject's mandible in a removable fashion. For example, the anchoring structure 14a and 14b can each include one or more loops to secure the oropharynx appliance 10 to the two or more teeth, portions of the gum, portions of the tongue, and/or portions of the mandible. In another example, the anchoring structure 14a and 14b can include magnets configured to attach to a reciprocal magnetic member that is connected to a portion of the subject's mouth. In some instances, the oropharynx appliance 30, as shown in FIG. 9, can include one or more springs 32a and 32b extending from the anchoring structures 14a and 14b. Although one spring 32a or 32b is shown as part of one anchoring structure 14a and 14b, two or more springs can be attached to each anchoring structure 14a and 14b to allow for greater movement of the tongue for swallowing and a stronger attachment of the passive tongue retention structure 12 to the anchoring structures 14a and 14b.

Figure 11:
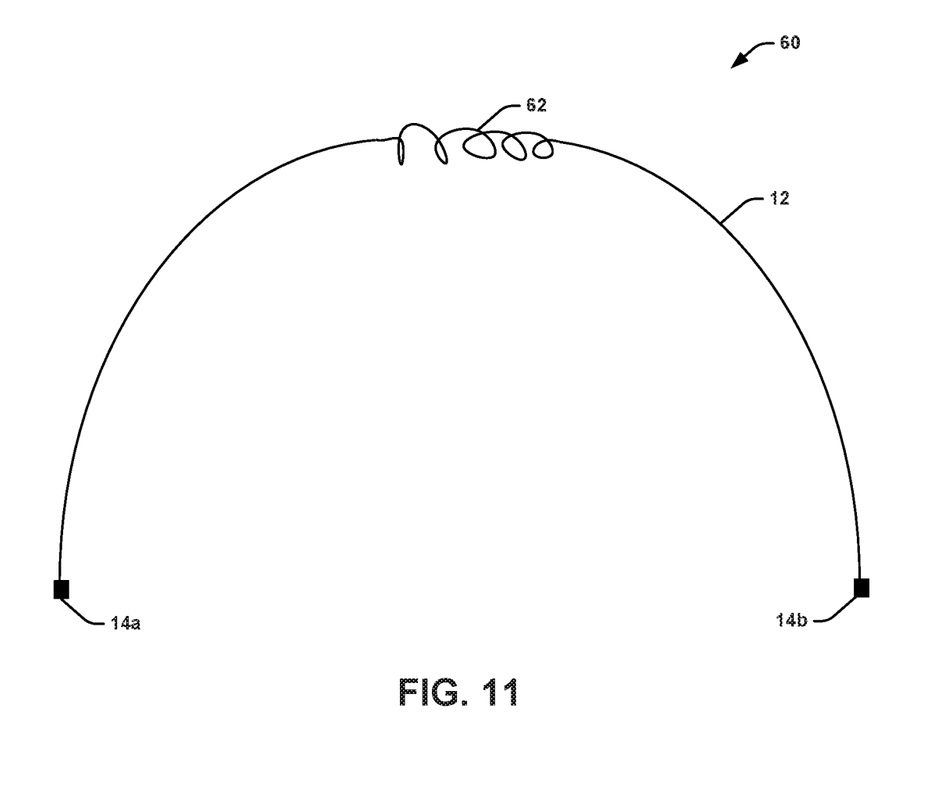
Figure 12:
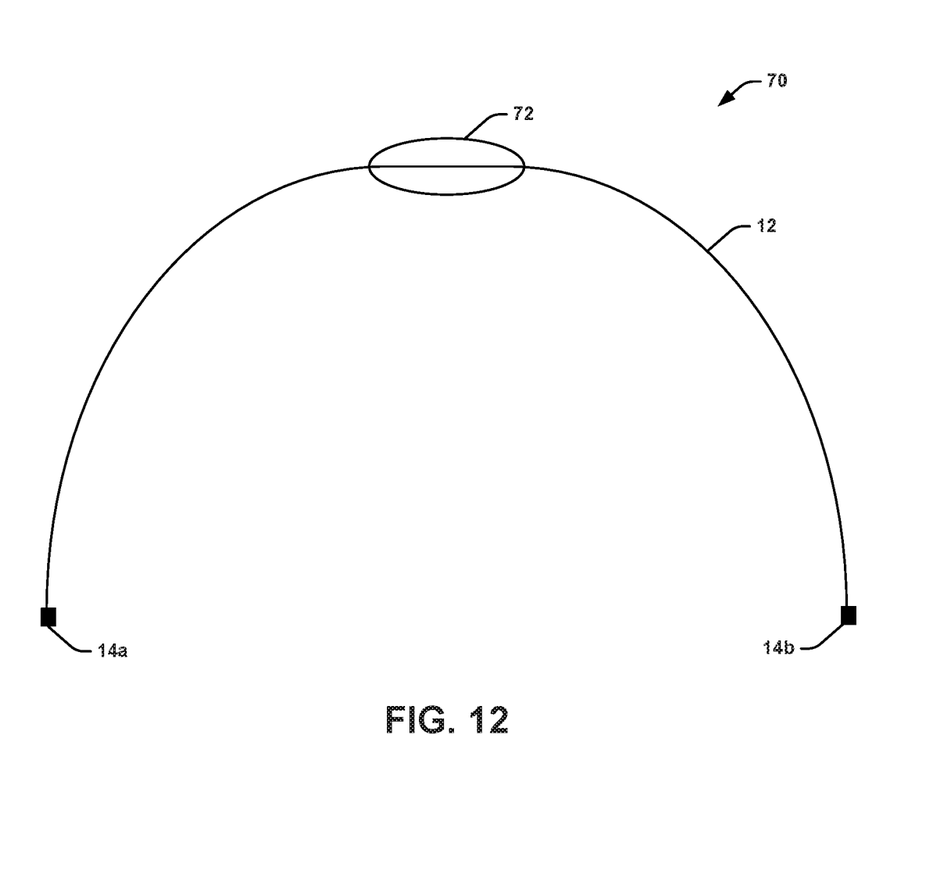

In another aspect, the end portion 16 can be adapted to contact a posterior pharyngeal portion of the subject's tongue. The passive tongue retention structure 12 can be sized and dimensioned so that the end portion 16 prevents the posterior pharyngeal portion of the tongue from obstructing the subject's oropharynx during sleep, without triggering the gag reflex, while still permitting the tongue to move during swallowing. As shown in the oropharynx appliance 40 of FIG. 10, the end portion 16 can include an engagement structure 42 that is configured to establish contact with the posterior pharyngeal portion of the tongue. In some instances, the engagement structure 42 can have a cross-sectional area larger than the rest of the passive tongue retention structure 12 to prevent the tongue from obstructing the oropharynx. For example, the engagement structure 42 can be in the form of one or more wire coils 62, as shown in FIG. 11. The engagement structure 42 can be of the same or different biocompatible material as the wire of the passive tongue retention structure 12. As a further example, the engagement structure 42 can be an additional portion of the same or different wire attached to the passive tongue retention structure 12. In another example, the engagement structure 42 can include a piece of material 72, FIG. 12, either the same as the wire or different from the wire. The engagement structure 42 can provide an additional surface area to prevent the tongue from moving backwards into the oropharynx during inspiration and obstructing the airway, while not generating the gag reflex and not generating an excess amount of saliva. The engagement structure 42, in some instances, can be used in combination with the springs 32a and 32b in an oropharynx appliance.

As an example, the passive tongue retention structure 12 need not be straight, as illustrated. Instead, the passive tongue retention structure 12 can be bent caudally by a small amount. Additionally, use of one or more springs 32a, 32b can be replaced by two earth magnets sliding into a groove. Moreover, the device need not contact the back of the tongue if one or more magnets are implanted in the tongue.

In some instances, the passive tongue retention structure 12 of the oropharynx appliance, as described herein with respect to FIGS. 1-12, can mate with a dental appliance that includes the anchoring structure 14 or structures. In other instances, the oropharynx appliance, as described herein with respect to FIGS. 1-12, can mate with an anchoring system of a dental appliance to form a system that prevents obstructive sleep apnea, such that a portion of the oropharynx appliance is secured in a predefined anatomical position. The dental appliance can be, for example, a mouthguard, a retainer, a crown, or the like. The dental appliance can be fitted to at least a portion of the subject's mouth (e.g., at least a portion of the mandible). Additionally, in some instances, the dental appliance can be removable from the subject's mouth.

Figure 13:
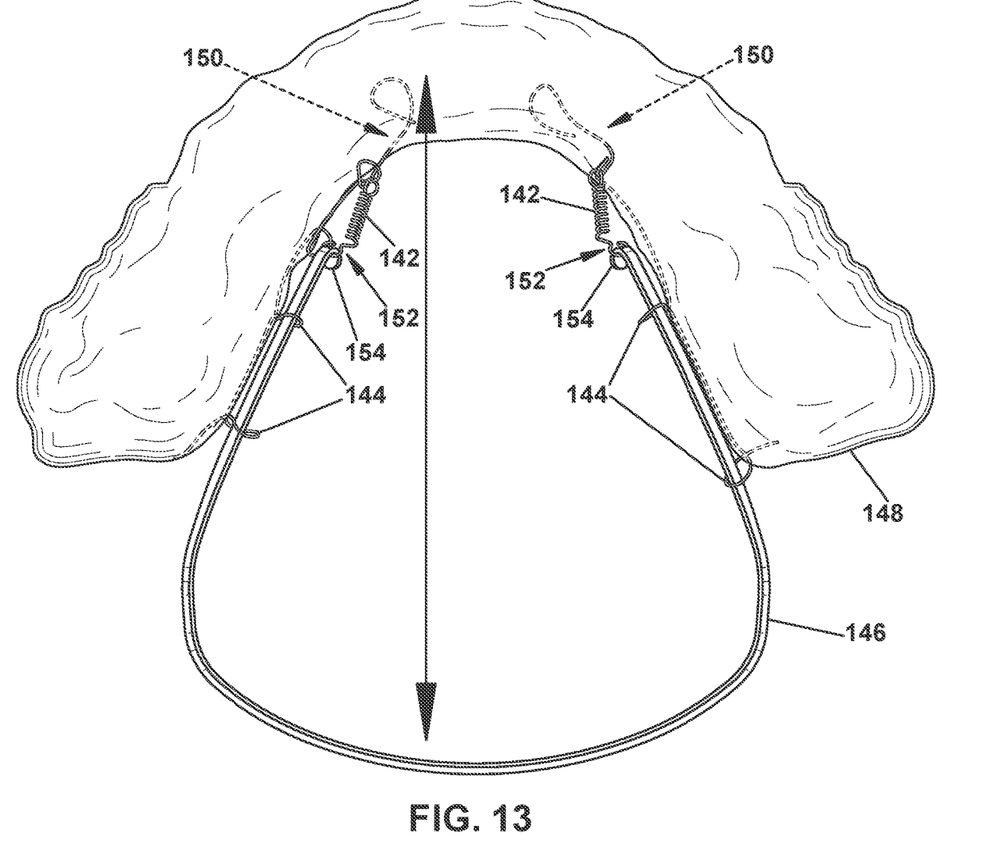
FIG. 13 is a photograph showing the oropharynx appliance of FIG. 8 attached to a mouthguard.
Figure 14:
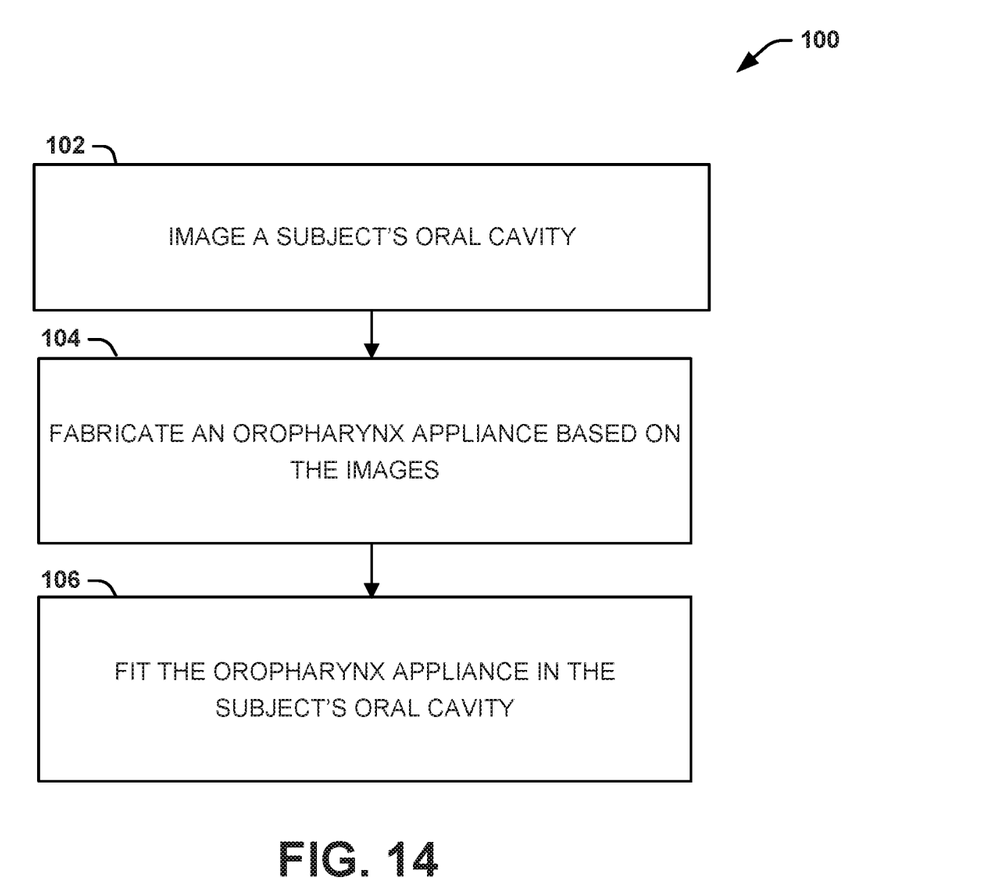
FIG. 14 is a process flow diagram showing a method for fitting an oropharynx appliance into a subject's oral cavity in accordance with another aspect of the present disclosure.

FIG. 13 illustrates an example system for preventing sleep apnea (similar to the system in FIG. 1). Advantageously, the system shown in FIG. 13 can prevent movement of the tongue into the oropharynx and, therefore, is ideal for patients with obstructive sleep apnea or excessive snoring (which is often thought of as a precursor to obstructive sleep apnea). The system shown in FIG. 13 allows a preset clearance of about 5-10% of the maximum distance between the wire and the teeth.

As shown in FIG. 13, the system can include a mouth guard 148 for the lower jaw, a wire 146, two springs 142, anchoring systems at the end of the spring, and an anchoring system and loops 144 (e.g., fixation structures) to hold the wire. As shown, the anchoring systems at the end of the spring can include anchors 150 embedded in the lingual side of the mouthguard 148 adjacent the position where a right and left incisor would be when the mouthguard is worn. The anchors 150 can connect the springs 142 to the mouthguard 148. The anchoring systems can also include a mating connection 152, which can be detachable, between the ends of the springs 142 (shown as loops) and the hooks 152 at the first and second ends of the wire 146, respectively. Additional features of the system can include a tube that holds the springs 142 and/or the wire 146 placed inside the mandible, further components to allow for better engagement of the tongue, and/or a spring-loaded telescoping system to eliminate the spring. In use, the system can be placed in the subject's mouth at night like a regular mouth guard. The system is fitted to the subject's mouth and the mouthguard 148 fits tightly onto the lower teeth. The system can prevent any obstruction during sleep while the tongue muscles are relaxed from the lack of muscle tone. The natural movement of the tongue into the oropharynx can be prevented by the springs 142 that resist the tongue's weight. Thus, in some instances, the spring specifications can be adjusted to the subject's tongue mass so that the subject can swallow any saliva generated at any time. The system can be removed in the morning and cleaned with methods similar to those used for false teeth.

IV. Methods

Another aspect of the present disclosure can include a method 100 (FIG. 13) for fitting an oropharynx appliance (for example, any oropharynx appliance as illustrated in FIGS. 1-12) into a subject's oral cavity. The method 100 can be used to personalize the oropharynx appliance for a particular subject. At 102, one or more images can be taken of a subject's oral cavity. The images can be taken at a plurality of different orientations. The images can be taken with any kind of two-dimensional or three-dimensional imaging modality that allows for visualization of the oral cavity, including x-ray, CT, or MRI. One example imaging modality can be a cone beam CT imaging modality. At 104, an oropharynx appliance can be fabricated based on the images. A mouthguard can be fabricated using standard dental practice, such as acrylic or 3D-printing based on the one or more images of the subject's oral cavity. For example, the 3D-printing can be based on a cone beam CT image. Dimensions can be gathered from the image, including the maximum distance between the wire and teeth and the corresponding clearance. At 106, the oropharynx appliance (or system) can be fit into the subject's oral cavity. Any required alterations to the oropharynx appliance (or system) can be made at this time.

It will be appreciated that the oropharynx appliance (or system) need not be constructed specifically for a particular subject. In some instances, the oropharynx appliance (or system) can be sized and dimensioned based on certain average mouth and/or tongue dimensions (e.g., based on anatomical averages for a particular population of subjects). The personalization can take place similarly to step 106 of method 100. However, in other instances, the personalization can take place at home by the subject by adjusting one or more features of the oropharynx appliance (or system) based on personal comfort.

From the above description, those skilled in the art will perceive improvements, changes and modifications. Such improvements, changes and modifications are within the skill of one in the art and are intended to be covered by the appended claims.

The following is claimed:

1. An oropharynx appliance configured to attach to a mandibular mouthguard, the oropharynx appliance comprising: a wire configured to extend from a first end point to a second end point in an arc shape in a plane parallel to a mandible of a subject and behind and in contact with at least a portion of the pharyngeal portion of a tongue of the subject; a first anchoring structure; and a second anchoring structure opposed to the first anchoring structure, each of the first anchoring structure and the second anchoring structure comprising a first assembly that is connected to the first end point and the second end point, respectively, and a second assembly connected to the first assembly to secure the wire to the mouthguard and configured to be positioned proximal to the mandible of the subject, wherein the first and second anchoring structures allow movement of the wire; wherein the wire is sized and dimensioned to prevent a posterior pharyngeal portion of the tongue from collapsing and obstructing an oropharynx of the subject during sleep, while still permitting the tongue to move during swallowing, wherein the first assembly of at least one of the first anchoring structure or the second anchoring structure comprises at least one resilient device that returns to its former shape when released after being pressed or pulled, wherein the second assembly comprises an anchor embedded in a lingual side of the mouthguard configured adjacent a right and left incisor of the subject, respectively, and to anchor the wire to the mouthguard.

2. The oropharynx appliance of claim 1, wherein the second structure further comprises a fixation structure configured to minimize up and down movement of the wire under a weight of the tongue.

3. The oropharynx appliance of claim 2, wherein the fixation structure is attached to a portion of the mouthguard and comprises loops configured to hold the wire.

4. The oropharynx appliance of claim 1, wherein a distal portion of the wire comprises an engagement structure configured to further contact a surface of a posterior pharyngeal portion of the tongue.

5. The oropharynx appliance of claim 1, wherein at least a portion of the wire is coated with a biocompatible material.

6. The oropharynx appliance of claim 1, wherein the wire comprises at least one of a biocompatible metal, a biocompatible polymer, and an organic material.

7. The oropharynx appliance of claim 1, wherein the first and second anchoring structures are physically spaced apart from one another.

8. A system comprising: a mouthguard configured to fit over at least a portion of a mandible of a subject; and an oropharynx appliance, configured to attach to the mouthguard, comprising: a wire extending between a first end and a second end, wherein the wire extends in an arcing shape between the first end and the second end along a lingual side of the mandible of the subject in a plane parallel to the mandible and behind and in contact with at least a portion of a posterior pharyngeal portion of a tongue of the subject to prevent the posterior pharyngeal portion of the tongue from collapsing and obstructing an oropharynx of the subject, an anchoring system comprising a first anchoring structure and a second anchoring structure attaching the first end and the second end of the wire to the mouthguard configured to be positioned at a right and left incisor of the subject, respectively, and to removably attach the wire to the mouthguard wherein each of the first anchoring structure and the second anchoring structure comprise: a first assembly comprising at least one resilient device that returns to its former shape when released after being pressed or pulled and a mating connector between the at least one resilient device and the first end and second end of the wire, respectively, and a second assembly comprising an anchor lingually connected to the mouthguard configured near the right and left incisor of the subject, respectively, and a fixation structure configured to minimize movement of the wire under a weight of the tongue.

9. The system of claim 8, wherein the anchoring system is configured to force a portion of the wire to extend along the lingual side of the subject's mouth.

10. The system of claim 8, wherein the fixation structure is attached to a portion of the mouthguard and comprises loops configured to hold the wire.

11. The system of claim 8, wherein the fixation structure is attached to a portion of the mouthguard and comprises a tube configured to hold the wire.

12. A system configured to be placed into a mouth of a subject at night to prevent obstruction of a throat during sleep while tongue muscles are relaxed, comprising: a removeable mouthguard configured to fit over at least a portion of a mandible of the subject; and to be removed from the mouth of the subject when the subject is awake and an oropharynx appliance, attached to the mouthguard, comprising: a wire extending between a first end and a second end, wherein the wire extends between the first end and the second end in an arcing shape, wherein the wire extends along a lingual surface of the mandible of the subject in a plane parallel to the mandible and behind and in contact with at least a portion of a posterior pharyngeal portion of a tongue of the subject to prevent the posterior pharyngeal portion of the tongue from collapsing and obstructing an oropharynx of the subject, an anchoring system comprising a first anchoring structure and a second anchoring structure attaching the first end and the second end of the wire to the mouthguard and configured to be positioned at a right and left incisor of the subject, respectively, wherein each of the first anchoring structure and the second anchoring structure comprise: at least one resilient device that returns to its former shape when released after being pressed or pulled, a mating connector attached to the at least one resilient device and configured to connect the at least one resilient device and the first end and the second end of the wire, respectively, wherein the first end and the second end of the wire comprise hooks for attaching to the mating connector, an anchor positioned in the mouthguard configured near the right and left incisor of the subject, respectively, and lingually extending from the mouthguard and configured to connect the at least one resilient device to the mouthguard, and a fixation structure attached to a portion of the mouthguard and configured to minimize movement of the wire under a weight of the tongue by holding the wire.

13. The system of claim 12, wherein the fixation structure comprises loops configured to hold the wire.

* * * * *